(12) United States Patent
Mishima

(10) Patent No.: US 6,464,676 B2
(45) Date of Patent: Oct. 15, 2002

(54) DISPOSABLE DIAPER

(75) Inventor: Yoshitaka Mishima, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/782,777

(22) Filed: Feb. 13, 2001

(65) Prior Publication Data

US 2001/0016719 A1 Aug. 23, 2001

(30) Foreign Application Priority Data

Feb. 18, 2000 (JP) ........................................ 2000-046766

(51) Int. Cl.[7] ................................................ A61F 13/15
(52) U.S. Cl. ............................ 604/385.19; 604/385.01; 604/358
(58) Field of Search ................................ 604/317–402, 604/358, 385.03, 385.01

(56) References Cited

U.S. PATENT DOCUMENTS

| | | | | |
|---|---|---|---|---|
| 4,753,645 A | * | 6/1988 | Johnson ...................... | 604/378 |
| 5,417,680 A | * | 5/1995 | Kimura et al. ............ | 604/385.2 |
| 5,489,282 A | * | 2/1996 | Zehner et al. ............ | 604/385.1 |
| 6,146,368 A | * | 11/2000 | Lapointe .................... | 604/385.1 |
| 6,160,198 A | * | 12/2000 | Roe et al. ................... | 604/361 |
| 6,177,606 B1 | * | 1/2001 | Etheredge et al. ......... | 604/378 |
| 6,328,724 B1 | * | 12/2001 | Ronnberg et al. ....... | 604/385.24 |
| 6,346,097 B1 | * | 2/2002 | Blaney ........................ | 604/327 |

FOREIGN PATENT DOCUMENTS

| | | |
|---|---|---|
| EP | 0955028 | 11/1999 |
| JP | 6-11723 | 2/1994 |
| JP | 08196565 | 8/1996 |
| WO | WO 9960975 | 12/1999 |

* cited by examiner

Primary Examiner—Jeanette Chapman
(74) Attorney, Agent, or Firm—Baker & Daniels

(57) ABSTRACT

A disposable diaper is provided on its inner side with an opening extending across a crotch region into a rear waist region over a predetermined area of a core and being normally biased to protrude from the inner surface of the diaper. The opening comprises a pair of cushioning pad members spaced apart from each other and a pair of liquid-resistant side flaps spaced apart from each other transversely of the diaper and extending longitudinally of the diaper.

5 Claims, 4 Drawing Sheets

DISPOSABLE DIAPER

BACKGROUND OF THE INVENTION

This invention relates to a disposable diaper for absorption and containment of excretion discharged thereon.

Japanese Utility Model Application Publication No. 1994-11723A describes a disposable diaper comprising a liquid-pervious first topsheet, a liquid-impervious backsheet, a liquid-absorbent core disposed between these two sheets, and a liquid-resistant second topsheet lying on the outer surface of the first topsheet and having longitudinally opposite end portions joined to the first topsheet. The second topsheet is provided in a longitudinally middle zone thereof with an opening and, around this opening, a plurality of elastic members spaced apart one from another by a given dimension longitudinally of the diaper and extending transversely of the diaper are secured under tension to the second topsheet. Contraction of these elastic members causes the opening to be widened transversely of the diaper. The diaper is able to receive feces into this opening and to prevent feces from moving and spreading from this opening.

However, it is impossible for the diaper disclosed in this Publication to separate urine and feces discharged into the opening at once from each other and it is concerned that urine, loose passage and watery feces might be mixed together and even if feces are solid, the feces might be mixed with urine to loosen.

SUMMARY OF THE INVENTION

According to this invention, there is provided a disposable diaper having transversely opposite side edges and longitudinally opposite ends, comprising a liquid-pervious topsheet, a liquid-impervious backsheet and a liquid-absorbent core disposed therebetween to define a front waist region, a rear waist region and a crotch region extending therebetween.

The diaper further comprises an opening being defined over a predetermined area extending across the rear waist region into the crotch region on an inner surface of the diaper by a pair of cushioning pad members extending transversely of the diaper and spaced apart from each other longitudinally of the diaper and a pair of liquid-resistant side flaps extending longitudinally of the diaper and spaced apart from each other transversely of the diaper; the cushioning pad members protruding from the inner side of the diaper; the liquid-resistant side sheets having proximal edges joined to the inner surface of the diaper, distal edges lying inside the proximal edges and extending between the pad members, and longitudinally opposite end portions being contiguous to transversely opposite ends of each the pad members covering and joined to the inner surface of the diaper; and the distal edges being elastically stretchable longitudinally of the diaper.

In the disposable diaper according to this invention the pad members cooperate with the side flaps to provide the inner side of the diaper with the opening into which feces is directly discharged. The pad members and the side flaps function as barriers to prevent undesirable movement of urine into the opening and movement of feces outward from the opening and thereby to prevent urine and feces discharged at once from being intermixed.

The pad member lying in the rear waist region can bear against the wearer's coccyx substantially in conformity with the recess of the coccyx while the pad member lying in the crotch region can bear against the wearer's crotch substantially in conformity with its shape. With an advantageous consequence, there is no anxiety that gaps or passages for urine and/or feces might be formed between the diaper and the wearer's skin. Additionally, the pad members have a sufficiently high cushioning property to avoid a possibility that these pad members might become bulky along their base edges and oblique edges as well as at their transversely opposite end portions. In this way, the diaper can be worn without any feeling of incompatibility.

DETAILED DESCRIPTION OF THE PREFERRED EMBODIMENTS

Details of a disposable diaper according to this invention will be more fully understood from the description given hereunder with reference to the accompanying drawings.

Figure 1:
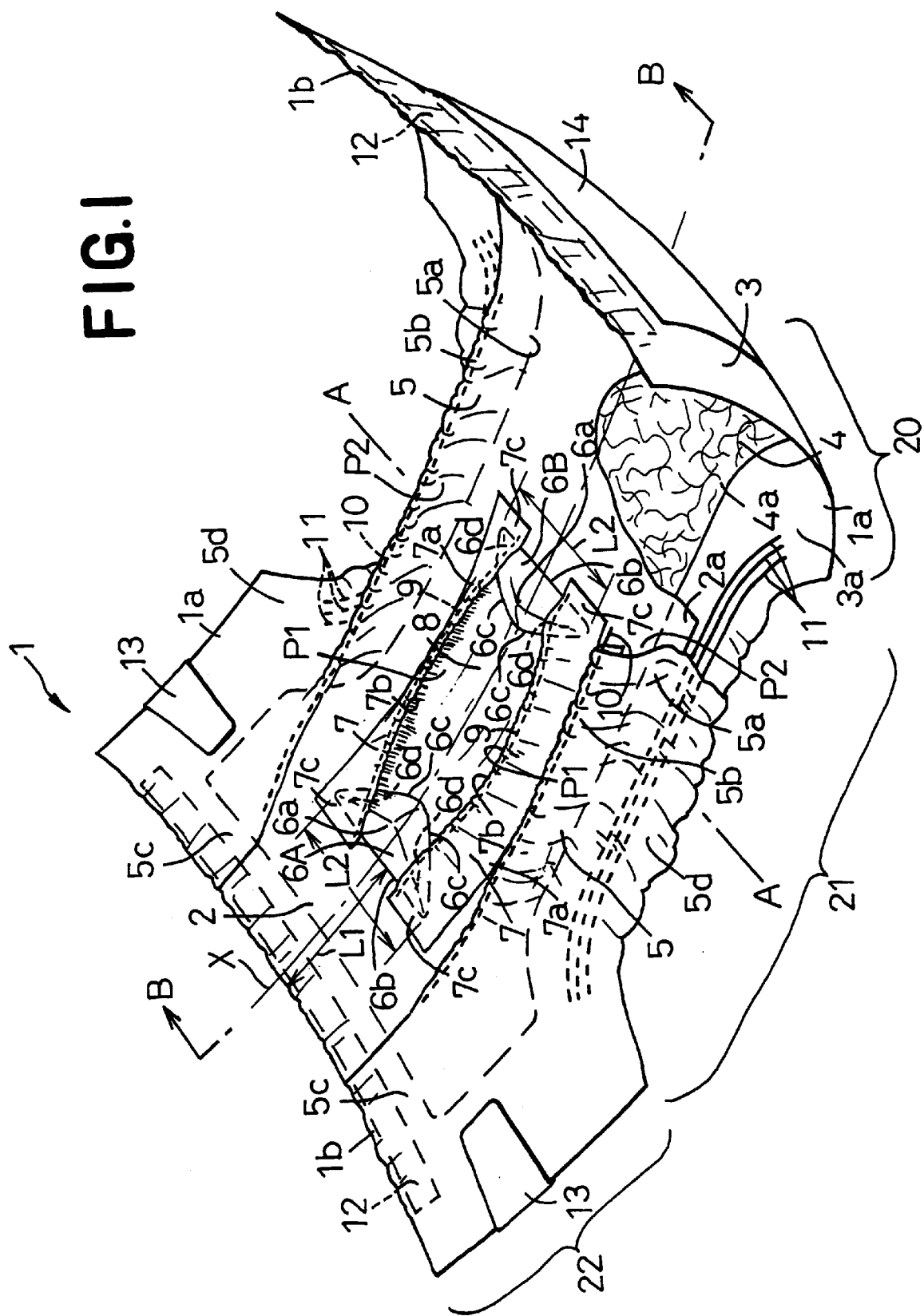
FIG. 1 is a perspective view depicting one embodiment of a partially cutaway disposable diaper according to this invention.

FIG. 1 is a perspective view depicting one embodiment of a partially cutaway disposable diaper according to this invention. The diaper 1 comprises a liquid-pervious topsheet 2, a liquid-impervious backsheet 3 and a liquid-absorbent core 4 disposed between the topsheet 2 and the backsheet 3. The diaper 1 is longitudinally configured by a front waist region 20, a rear waist region 22 and a crotch region 21 extending between the front and rear waist regions 20, 22. The diaper 1 is contoured by transversely opposite side edges 1a extending in parallel to each other longitudinally of the diaper 1 and describing in the crotch region 21 circular arcs, respectively, which are convex inwardly of the diaper 1, on one hand, and longitudinally opposite ends 1b extending in parallel to each other transversely of the diaper 1, on the other hand. In the vicinity of the side edges 1a of the diaper 1 is provided with a pair of liquid-resistant leak-barrier cuffs 5 which are spaced apart from and extend in parallel to each other longitudinally of the diaper.

The diaper 1 further comprises a pair of cushioning pad members 6A, 6B and a pair of liquid-resistant side flaps 7. Each of the cushioning pad. members 6A, 6B is normally biased to protrude from the inner side of the diaper 1 and extending transversely of the diaper 1. Each of the liquid-resistant side flaps 7 extends longitudinally of the diaper 1 and is normally biased to rise on the inner side of the diaper 1. The pair of cushioning pad members 6A, 6B cooperate with the pair of liquid-resistant side sheets 7 to define an opening 8 over a region of the core 4 extending across the crotch region 21 into the rear waist region 22.

The pad members 6A, 6B lie inside the respective leak-barrier cuffs 5 and are spaced apart from each other by a desired dimension longitudinally of the diaper 1 so that the respective pad members 6A, 6B may positioned above the core 4 in the crotch region 21 and the rear waist region 22, respectively. Each of these pad members 6A, 6B has the maximum height L3 (See FIG. 2) larger than a height of a free end 7b of the side sheet 7 substantially at its central zone 6a. Each of the pad members 6A, 6B is configured to define surfaces obliquely descending from its central zone 6a toward its peripheral edge.

The pad member 6A lying in the rear waist region 22 has a base edge 6b transversely extending in adjacency to the outer end 1b of the rear waist region 22, a pair of oblique edges 6c extending from transversely opposite ends of the base edge 6b toward the crotch region 21 and progressively approaching each other as they extend toward the crotch region 21, and transversely opposite end portions 6d at which the base edge 6b intersects the pair of oblique edges 6c. The pair of oblique edges 6c intersect each other in the vicinity of a longitudinal center line X bisecting a dimension between the side edges 1b of the diaper 1. A dimension L1 of the pad member 6A as measured from the outer end 1b of the rear waist region 22 to the base edge 6b of the pad member 6A is preferably in a range of 60~120 mm, more preferably in a range of 80~100 mm.

The pad member 6B lying in the crotch region 21 has a base edge 6b transversely extending in adjacency to the front waist region 20, a pair of oblique edges 6c extending from transversely opposite ends of the base edge 6b toward the rear waist region 22 and progressively approaching each other as they extend toward the rear waist region 22, and transversely opposite end portions 6d at which the base edge 6b intersects the pair of oblique edges 6c. The pair of oblique edges 6c intersect each other in the vicinity of a longitudinal center line X bisecting a dimension between the side edges 1b of the diaper 1. A dimension L2 of the base edge 6b in both the pad member 6A and the pad member 6B is preferably in a range of 50~80 mm.

The side flaps 7 lie inside the respective leak-barrier cuffs 5 and are spaced apart from each other by a dimension transversely of the diaper 1 in contiguousness to the respective transversely opposite end portions 6d of the respective pad members 6A, 6B. Each of the side flaps 7 has a proximal edge 7a joined to the outer surface of the topsheet 2 and extending longitudinally of the diaper 1, a distal edge 7b lying inside the proximal edge 7a and longitudinally extending between the pad members 6A, 6B, and longitudinally opposite ends 7c covering the transversely opposite ends 6d of the respective pad members 6A, 6B. These longitudinally opposite ends 7c are collapsed inwardly of the diaper 1 and joined to the transversely opposite ends 6d of the respective pad members 6A, 6B and to the outer surface of the topsheet 2 in such collapsed state. A longitudinally extending elastically stretchable member 9 is secured under tension to the distal edge 7b in the manner that the elastically stretchable member 9 is covered with a part of the distal edge 7b.

The leak-barrier cuffs 5 lie in the vicinity of the transversely opposite side edges 4 of the core 4, each having a proximal edge 5a joined to the outer surface of the topsheet 2 and extending longitudinally of the diaper 1, a distal edge 5b extending inward transversely of the diaper 1 in the crotch region 21 and normally biased to rise on the diaper 1, and longitudinally opposite ends 5c collapsed inward transversely of the diaper 1 and joined to the outer surface of the topsheet 2 in the front and rear waist regions 20, 22 in such collapsed state. A longitudinally extending elastically stretchable member 10 is secured under tension to the distal edge 5b of the leak-barrier cuff 5 in the manner that the elastically stretchable member 10 may be covered with a part of the distal edge 5b.

The diaper 1 is provided along the transversely opposite side edges 1a with thread-like elastic members 11 secured under tension thereto in association with leg-openings and along the longitudinally opposite ends with film-like elastic members 12 secured under tension thereto in association with a waist-opening. In the rear waist region 22, proximal ends of tape fasteners 13 are attached to the transversely opposite side edges 1a so that these fasteners 13 extending inward transversely of the diaper 1 from the respective side edges 1b. In the front waist region 20, a rectangular strip of target tape 14 is attached to the outer surface of the backsheet 3 so that the tape fasteners 13 may be anchored on this strip of target tape 14.

The diaper 1 is longitudinally curved with its inner surface inside and the elastic members 9, 10, 11, 12 have been relaxed to generate a plurality of gathers along the distal edge 7b of the respective side flaps 7, the distal edge 5b of the respective leak-barrier cuffs 5 and the transversely opposite side edges 1a as well as the longitudinally opposite ends 1b of the diaper 1. The side flaps 7 cooperate with the topsheet 2 to form a pair of pockets P1 opening inward transversely of the diaper 1 while the leak-barrier cuffs 5 cooperate with the topsheet 2 to form a pair of pockets P2 opening also inward transversely of the diaper 1.

The tape fasteners 13 may be anchored on the strip of target tape 14 by means of pressure-sensitive adhesive coating the inner surface of the free end portions thereof to form the pair of leg-openings and the waist-opening (not shown).

Figure 2:
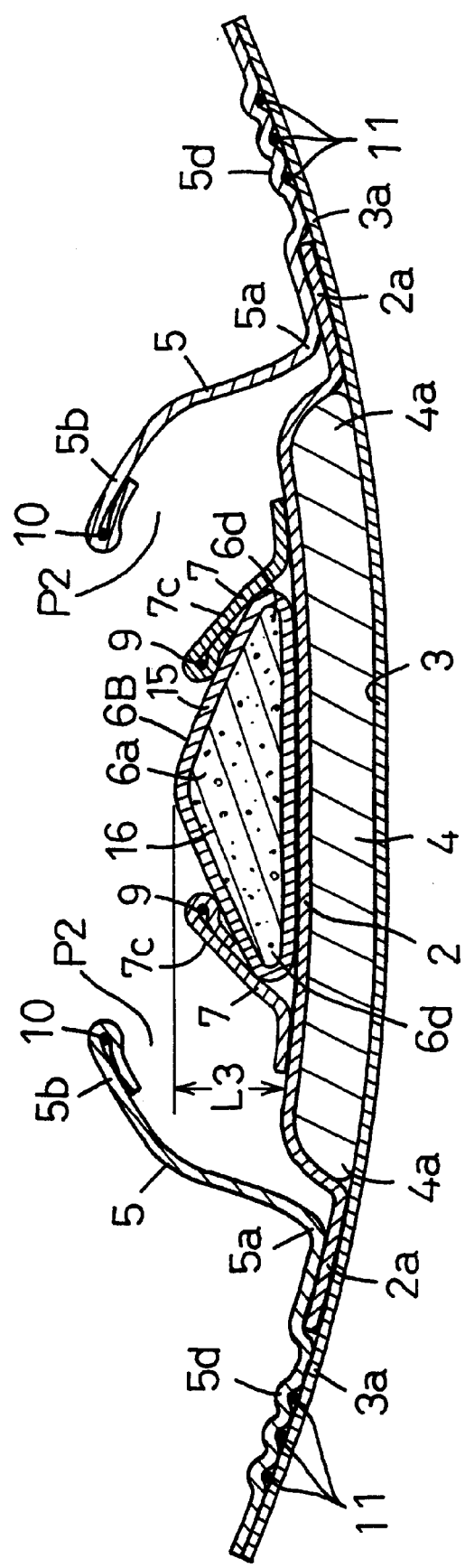
FIG. 2 is a sectional view taken along line A—A in FIG. 1.
Figure 3:
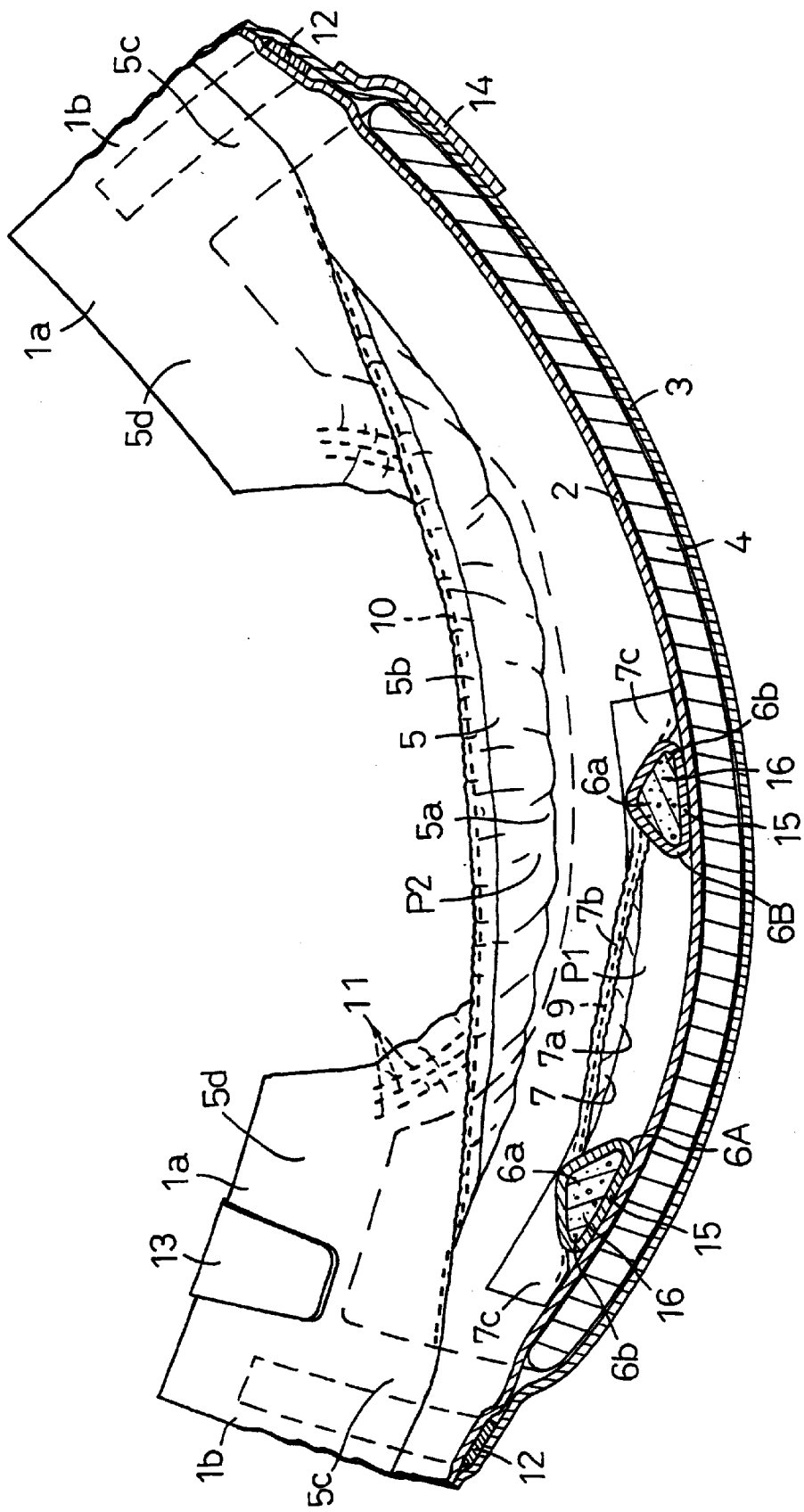
FIG. 3 is a perspective view depicting the diaper partially in a sectional view taken along line B—B in FIG. 1.

FIG. 2 is a sectional view taken along line A—A in FIG. 1 and FIG. 3 is a perspective view depicting the diaper partially in a sectional view taken along line B—B in FIG. 1. The pad members 6A, 6B are formed with liquid-absorbent elastic material 15 and liquid-pervious nonwoven fabric 16 wrapping the elastic material 15. Each of the pad members 6A, 6B has its bottom surface joined to the outer surface of the topsheet 2. The height L3 of the respective pad members 6A, 6B is preferably in a range of 10~30 mm as measured from the bottom surface to the central zone 6a. Preferably, the pad members 6A, 6B have a compressive elastic recovery of 50% or higher, which is higher than that of the core 4.

As will be seen in FIG. 2, transversely opposite side edge portions 2a of the topsheet 2 extend laterally outward slightly beyond transversely opposite side edges 4a of the core 4. Transversely opposite side edge portions 3a of the backsheet 3 as well as outer side portions 5d of the leak-barrier cuffs 5 extend laterally outward beyond the side edge portions 2a of the topsheet 2. Each of the side edge portions 2a is disposed between the side edge portion 3a of the backsheet 3 and the outer side portion 5d of the leak-barrier cuff 5, respectively, and joined to the inner surface of at least one of the backsheet 3 and the leak-barrier cuffs 5. The side edge portions 3a of the backsheet 3 and the outer side portions 5d of the leak-barrier cuffs 5 are put flat and joined together.

The elastic members 11 associated with the leg-openings are disposed between the transversely opposite side edge portions 3a of the backsheet 3 and the outer side portions 5d of the leak-barrier cuffs 5 and bonded to the inner surface of at least one of the backsheet 3 and the leak-barrier cuffs 5. The elastic members 12 associated with the waist-opening are disposed between the topsheet 2 and the backsheet 3 and joined to the inner surface of at least one of these two sheets 2, 3. The core 4 is joined to the inner surface of at least one of the top- and backsheets 2, 3.

Figure 4:
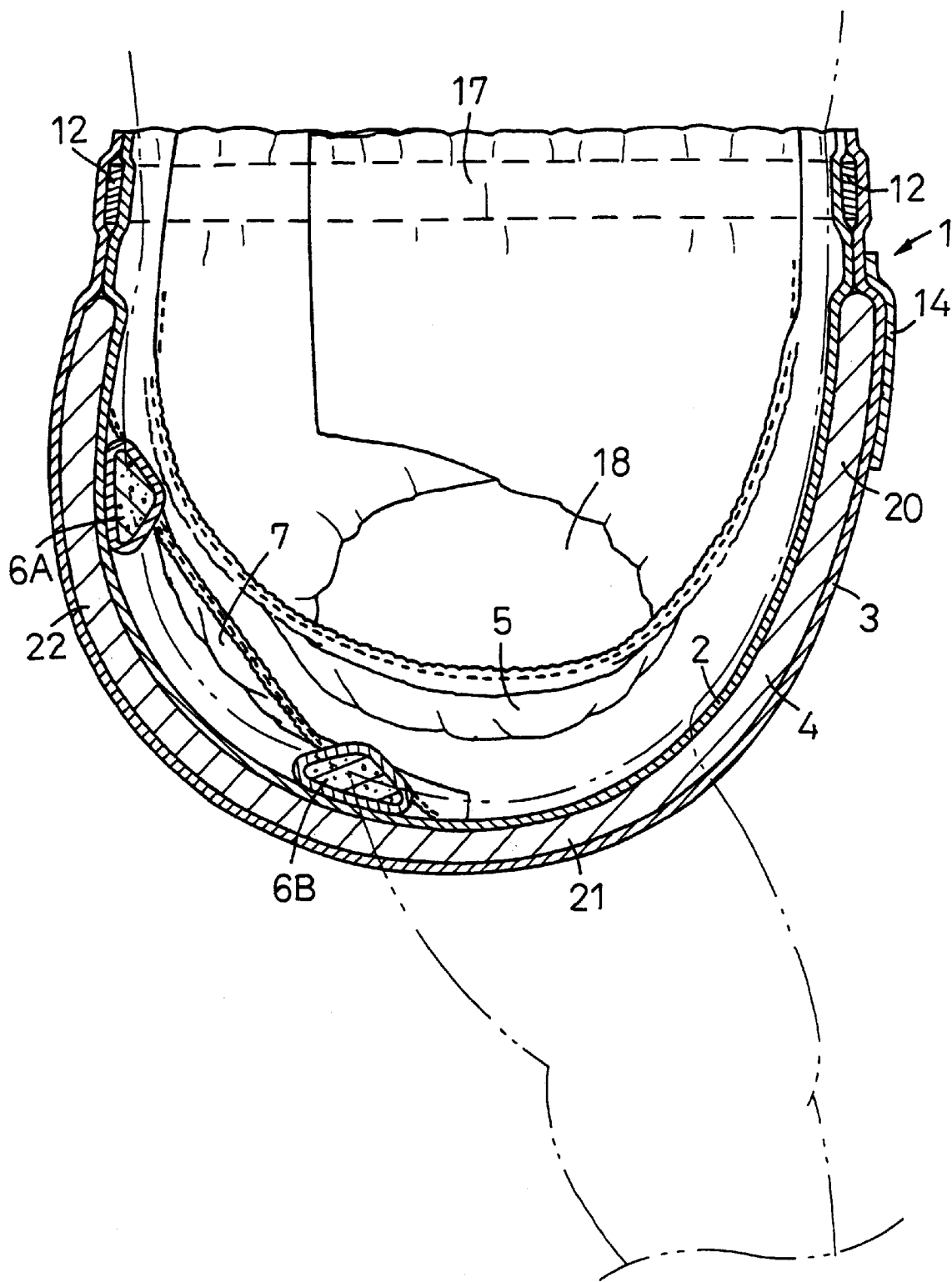
FIG. 4 is a side view depicting the diaper as put on a wearer's body.

FIG. 4 is a side view depicting the diaper as put on a wearer's body indicated by chain lines. Of the diaper 1, the pad member 6A lying in the rear waist region 22 bears against the wearer's coccyx and the pad member 6B lying in the crotch region 21 bears against the wearer's crotch. Feces discharged into the opening 8 of the diaper 1 is absorbed by the core 4 through the topsheet 2 while urine discharged on the front waist-region 20 of the diaper 1 is also absorbed by the core 4 through the topsheet 2. Even if a certain amount of urine spreads on the outer surface of the topsheet 2 until it reaches the rear waist region 22, the pad members 6 and the side flaps 7 function as barriers to prevent such amount of urine from flowing into the opening 8. The topsheet 2 is exposed between the respective leak-barrier cuffs 5 and the respective side flaps 7 so that the amount of urine flowing between the respective leak-barrier cuffs 5 and the respective side flaps 7 may be absorbed also in the crotch region 21 and the rear waist region 22.

Each of the pad members 6A, 6B presents a substantially conical shape having its apex defined by the substantially central zone 6a and obliquely descending from the central zone 6a to the peripheral edge of the pad member. As viewed in the plan view, each of the pad members 6A, 6B presents a triangular shape having the base edge 6b and the pair of oblique edges 6c. Such configuration enables the pad member 6A to bear against the wearer's coccyx substantially in conformity with a recess of the coccyx and enables the pad member 6B to bear against the wearer's crotch substantially in conformity of its shape. With an advantageous consequence, there is no anxiety that gaps or passages for urine and/or feces might be formed between the diaper 1 and the wearer's skin. Additionally, the pad members 6A, 6B have a sufficiently high cushioning property to avoid a possibility that these pad members 6A, 6B might become bulky along their base edges 6b and oblique edges as well as at their transversely opposite end portions 6d. In this way, the diaper 1 can be worn without any feeling of discomfort.

With the diaper 1 according to this invention, the pad members 6A, 6B are able to absorb an amount of excretion before this amount of excretion might flow beyond these pad members 6A, 6B. Such function of the pad members 6A, 6B makes it further reliable to prevent feces and urine from being mixed together. The amount of excretion having been absorbed by the pad members 6A, 6B is then absorbed by the core 4 through the topsheet 2.

The elastic members 15 as the component of the pad members 6A, 6B are preferably formed with polyurethane foam of open cell type in view of its high flexibility and liquid-absorbency. The elastic members 15 may be formed with the material other than the polyurethane foam, for example, tow obtained by steps of filamentating initial tow comprising a plurality of continuous filaments, then bundling them together into a rod-like condition and cutting it into a desired length; a hydrophilic fibrous assembly merely crimping-treated; or a nonwoven fabric comprising individual fibers loosely intertwined.

The topsheet 2 may be formed with a liquid-pervious sheet such as a nonwoven fabric or a pored plastic film, preferably by a liquid-pervious hydrophilic sheet. The backsheet 3 may be formed with a hydrophobic nonwoven fabric, a liquid-impervious plastic film or a laminated sheet consisting of a hydrophobic nonwoven fabric and a plastic film, preferably by a breathable but liquid-impervious sheet. The leak-barrier cuffs 5 and the side sheets 7 may be formed with a breathable but liquid-impervious nonwoven fabric.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. It is also possible to use, as the stock material for the backsheet 3, the leak-barrier cuffs 5 and the side sheets 7, a composite nonwoven fabric (SMS nonwoven fabric) comprising a melt blown nonwoven fabric having a high water-resistance of which the opposite sheet surfaces are sandwiched between sheet surfaces of a melt blown nonwoven fabric having a high strength and a high flexibility. The component fiber may be selected from a group including polyolefine, polyester and polyamide fibers and conjugated fiber of polyethylene/polypropylene or polyester.

The core 4 may be formed by a mixture of fluff pulp and high absorption polymer grains compressed to a desired thickness and then entirely covered with a water-pervious sheet (not shown) such as tissue paper. Bonding or attachment of the core 4, the elastic members 9, 10, 11, 12 and the sheets 2, 3, 5, 7 may be carried out using suitable adhesive such as hot melt adhesive or pressure-sensitive adhesive or heat-sealing technique.

This invention is applicable not only to the open type diaper 1 as illustrated but also to the pants-type diaper in which the front and rear waist regions are previously joined together along their transversely opposite side edge portions.

What is claimed is:

1. A disposable diaper having transversely opposite side edges and longitudinally opposite ends, said diaper comprising:

a liquid-pervious topsheet;

a liquid-impervious backsheet;

a liquid-absorbent core disposed between said liquid-pervious topsheet and said liquid-impervious backsheet;

a front waist region;

a rear waist region;

a crotch region extending between the front and rear waist region;

a pair of cushioning pad members extending transversely of said diaper and protruding from an inner side of said diaper that are spaced apart from each other longitudinally of said diaper;

a pair of liquid-resistant side flaps that extend longitudinally of said diaper and are spaced apart from each other transversely of said diaper and have proximal edges joined to the inner surface of said diaper, distal edges lying inside said proximal edges and extending between the pair of cushioning pad members longitudinally of said diaper, and longitudinally opposite ends being contiguous to transversely opposite ends of each said cushioning pad member covering and joined to the inner surface of said diaper, said distal edges being elastically stretchable longitudinally of said diaper; and an opening provided over an area extending across said rear waist region into said crotch region of the inner surface of said diaper, said opening defined by said pair of cushioning pad members and said pair of liquid-resistant side flaps.

2. The diaper according to claim 1, wherein said pair of cushioning pad members have a maximum height substantially at central zones thereof which maximum height is larger than a height of said distal edges of said liquid-resistant side flaps, the pair of cushioning pad members having surfaces obliquely descending from said central zones toward respective peripheral edges thereof.

3. The diaper according to claim 1, wherein one pair member of said pair of cushioning pad members lies in said rear waist region and has a base edge transversely extending adjacently to an outer end of said rear waist region, a pair of oblique edges extending from transversely opposite ends of said base edge toward said crotch region and progressively approaching each other as they extend toward said crotch region, and transversely opposite end portions at which said base edge intersects said pair of oblique edges, said oblique edges intersecting each other in a vicinity of a longitudinal center line that bisects a dimension between said transversely opposite side edges of said diaper.

4. The diaper according to claim 1, wherein one pair member of said pair of pad members lies in said crotch region and has a base edge transversely extending adjacently to said front waist region, a pair of oblique edges extending from transversely opposite end portions of said base edge toward said rear waist region and progressively approaching each other as they extend toward said rear waist region, said pair of oblique edges intersecting each other in a vicinity of a longitudinal center that bisects a dimension between said transversely opposite side edges of said diaper.

5. The diaper according to claim 1, wherein said pair of pad members comprise liquid-absorbent elastic members and a liquid-pervious nonwoven fabric covering said liquid-absorbent elastic members.

* * * * *